(12) United States Patent
Delaney

(10) Patent No.: US 9,433,492 B2
(45) Date of Patent: Sep. 6, 2016

(54) METHOD AND DEVICE FOR FACILITATING SURGICAL ACCESS TO A BODY AREA

(75) Inventor: Jeffrey W. Delaney, Durham, NC (US)

(73) Assignee: Boarad of Regents of the University of Nebraska, Lincoln, NE (US)

( * ) Notice: Subject to any disclaimer, the term of this patent is extended or adjusted under 35 U.S.C. 154(b) by 1774 days.

(21) Appl. No.: 11/533,512

(22) Filed: Sep. 20, 2006

(65) Prior Publication Data

US 2010/0222869 A1    Sep. 2, 2010

(51) Int. Cl.
| A61B 19/00 | (2006.01) |
| A61F 2/06 | (2013.01) |
| A61B 17/00 | (2006.01) |
| A61B 17/11 | (2006.01) |

(52) U.S. Cl.
CPC ........ *A61F 2/06* (2013.01); *A61B 2017/00252* (2013.01); *A61B 2017/1139* (2013.01); *A61F 2002/061* (2013.01)

(58) Field of Classification Search
USPC .............................. 604/8, 9, 6.16, 507, 93.01
See application file for complete search history.

(56) References Cited

U.S. PATENT DOCUMENTS

| 5,125,904 A | 6/1992 | Lee |
| 5,167,637 A | 12/1992 | Okada et al. |
| 5,195,980 A | 3/1993 | Catlin |
| 5,269,771 A | 12/1993 | Thomas et al. |
| 5,312,355 A | 5/1994 | Lee |
| 5,385,541 A * | 1/1995 | Kirsch et al. ...................... 604/8 |
| 5,824,071 A * | 10/1998 | Nelson et al. ................ 606/194 |
| 5,895,404 A | 4/1999 | Ruiz |
| 5,911,710 A | 6/1999 | Barry et al. |
| 6,004,301 A | 12/1999 | Carter |
| 6,090,067 A * | 7/2000 | Carter ........................ 604/93.01 |
| 6,352,520 B1 | 3/2002 | Miyazaki |
| 6,652,567 B1 | 11/2003 | Deaton |
| 6,966,896 B2 | 11/2005 | Kurth et al. |

OTHER PUBLICATIONS

Fontan Operation.com, www.fontanoperation.com/fontan.htm.

* cited by examiner

*Primary Examiner* — Leslie Deak
(74) *Attorney, Agent, or Firm* — Advent, LLP

(57) ABSTRACT

A vascular graft that has a valve incorporated into a wall thereof is described. The graft may be used in gaining access to interior portions of the heart. The valve is normally closed and may be opened by a surgical device threaded into the vascular graft and to the valve. Surgical procedures may be performed within the heart with the access provided. Alternately, the valve may be placed in an open state to permit blood communication between the interior of the graft and the interior of the heart or in a closed state to prevent such communication. The vascular graft described has application in Fontan procedures and is useful in pediatric cardiac surgery and in further treating patients who have undergone Fontan procedures.

16 Claims, 6 Drawing Sheets

METHOD AND DEVICE FOR FACILITATING SURGICAL ACCESS TO A BODY AREA

FIELD OF THE INVENTION

This invention relates to the field of pediatric cardiac surgery, and more particularly to the treatment of various forms of congenital heart disease in children.

BACKGROUND OF THE INVENTION

Each year, 8 of every 1000 children born have some form of congenital heart disease which involves a malformation of a part of the heart. Approximately 10% of these cases are represented by malformations in which there is only one functional, well-formed, ventricular chamber in the heart of the infant. While most commonly described as a deficit of the right side of the heart in which the right ventricle and perhaps the right atrium are not well-formed, the deficit may occur on either side of the heart. The system for directing the venous return blood flow to the lungs for re-oxygenation and the flow of oxygenated blood to the body is severely impacted, as the blood must entirely mix within the heart. Without some form of palliative or reconstructive surgery nearly all such infants do not survive for more than a brief time. The most common treatment for this condition includes a series of surgeries commonly known collectively as the Fontan procedure. The outcome of the Fontan procedure is to direct the venous return flow of de-oxygenated blood directly into the pulmonary arteries and thence into the lungs, entirely bypassing the heart. Doing so entails relying on the central venous pressure and the negative thoracic pressure generated through inspiration to provide the motive force to move the returned blood through the lungs and into the left atrium of the heart where it begins its circulation back to the body. However, patients are enabled to live generally normal lives with proper medical care. That medical care, however, includes the high likelihood for requiring interventional access to the interior of the heart, and there are significant problems associated with gaining this access.

To better understand the problems with gaining needed interventional access to the heart, a brief discussion of the anatomy of the heart, as illustrated in the accompanying drawings, and the use of the Fontan procedure is in order. The heart H is the organ of the body which powers the circulation of blood within the body. Circulating blood within the body includes providing a sufficient flow of oxygenated blood to all parts of the body to, among other things, provide oxygen to the tissues and organs of the body. As the blood circulates within the tissues, it becomes de-oxygenated, or cyanotic, and is returned to the lungs where the blood is recharged with oxygen. The heart is a muscular organ which includes four pumping chambers to power this circulation. These chambers are the right atrium RA, the left atrium LA, the right ventricle RV and the left ventricle LV. The heart undergoes a rhythmic and sequenced contraction of first the atria and then the ventricles. It is convenient to begin the discussion with the right atrium RA. Returning cyanotic blood from the head and upper extremities enters the superior vena cava SVC, and blood returning from the lower organs and extremities enters the inferior vena cava IVC. Blood thus returned is ported from the venae cavae, SVC and IVC, into the right atrium RA. The pumping cycle of the heart begins with contraction of the right atrium RA, pressurizing blood contained therein such that the blood flows through the tricuspid valve into the right ventricle RV. Contraction of the right ventricle RV closes the tricuspid valve and forces the blood through the pulmonary valve, into the pulmonary arteries PA, and thence into the lungs. Blood passes through the lungs, primarily under the motive force of right ventricular contraction. The blood is oxygenated in the lungs and passes into the left atrium LA. Atrial contraction forces blood from the left atrium LA and through the mitral valve into the left ventricle LV. Ventricular contraction closes the mitral valve and forces the blood through the aortic valve, into the aorta A, and thence to the various parts of the body by means of the arterial system. The arterial system includes smaller arteries and capillaries allowing the blood to supply oxygen the tissues. The blood gradually becomes more cyanotic as it moves through the tissues and into the venules and larger veins of the venous system. The venous system returns the blood to the superior vena cava SVC and the inferior vena cava IVC and thence into the right atrium RA, completing a cycle. Blood moves through the venous system urged by general bodily muscle contractions which generally cyclically compress the veins. Aided by one way valves in the veins, such repeated contractions effectively push the blood back towards the heart H. Venous flow is further urged due to the continuing flow of blood from the left ventricle LV into and through the tissues by way of the arterial system. Blood pressure in the venous system is maintained generally low at least partially by the pumping action of the right side of the heart as blood is drawn into the right atrium RA from the venae cavae.

When an infant is born with certain forms of congenital heart disease, the above-described heart function and circulation is severely impacted. The functioning of one side of the heart may be severely limited or non-existent. Mediation of this condition generally involves a first surgery which provides a small arterial shunt of blood to the lungs. This provides limited but adequate blood flow for the infant to grow and for the lung vasculature to mature and be ready for a second surgery. The second surgery includes disconnecting the superior vena cava SVC from the right atrium RA and connecting the superior vena cava to the superior aspect of the right pulmonary artery PA. This procedure, known as the bidirectional Glenn procedure, thus bypasses venous return flow from the head and upper extremities directly to the lungs. The pulmonary arteries PA are completely detached from the heart such that they essentially form one bi-directional artery connected between the inlets of the lungs. The outlet from the right ventricle RV is closed. During recuperation from the second surgery, the flow from the inferior vena cava IVC is allowed to continue into the malformed heart. After a further period of growth and recuperation, a third surgery is performed in which the flow from the inferior vena cava IVC is also directed into the pulmonary artery PA. This third surgery is particularly referred to as a Fontan operation while its combination with the Glenn procedure is collectively referred to as the Fontan procedure. In this third surgery, the connection of the inferior vena cava IVC to the right atrium RA is also severed and the inlet to the right atrium is closed such that the right side of the heart is entirely disconnected from the systemic venous return flow. Also the space within the right atrium RA is made contiguous with the space within the left atrium LA. The next step of the surgery is to attach the inferior vena cava IVC to the inferior aspect of the right pulmonary artery PA, thus perfecting a return path for venous blood from the lower body to the lungs. This connection, however, cannot be done with exclusively native tissue because the two vessels (pulmonary artery PA and interior vena cava IVC) are not located in close enough proximity to each other. A synthetic, generally tubular, vascular graft is used to make this connection. Two particular procedures currently used to implant this graft are the Lateral Tunnel Fontan and the External Conduit Fontan. Both procedures entail connecting a synthetic vascular tube graft between the proximal end of the inferior vena cava IVC and the inferior aspect of pulmonary arteries PA. In the case of the External Conduit Fontan, the graft lies outside and alongside the heart, while in the case of the Lateral Tunnel Fontan the graft passes through a tunnel surgically prepared in the right side of the heart. In either case, the synthetic tubular graft conducts returning cyanotic blood from the lower body directly to the pulmonary arteries. The Lateral Tunnel Fontan and the External Conduit Fontan thus provide the same function. Physicians choose one or the other type of Fontan based on anatomical/medical considerations and institutional preference. In either case, the interior of any vestigial atrium is made contiguous with the interior of the other, well-formed, atrium. Thus, the pumping action of the heart is undertaken entirely by rhythmic and sequenced atrial and ventricular contractions. More particularly, blood flowing into the heart from the lungs is forced by atrial contraction into the well-formed ventricle. The ventricle then contracts and pushes the blood into the aorta A and thence into the arterial circulation in all areas of the body. Blood moves into tissues of the body from the arterial system and leaves those tissues by way of the venous system, returning directly to the lungs and bypassing the heart.

Management of patients who have had Fontan procedures performed on their hearts is complicated by the fact that access to the heart from the venous system is made difficult if not impossible. Such patients have a high incidence of arrhythmia and other cardiac complications, and the treatment and intervention for such complications can require later access to the heart. The common way to reach the normal heart is through the pathway provided by the superior vena cava SVC or the inferior vena cava IVC using a catheter threaded from outside the body by way of the venous system to one of those areas and thence into the heart. However, that pathway is removed by the Fontan procedure. Often surgeons will create a fenestration, or opening, connecting the graft to the interior of the heart during the Fontan procedure. This is done to lower venous pressure and to make the pressure more stable in the early post-operative period. These fenestrations are unreliable and often close soon after surgery. If, however, the fenestration remains patent, at best the patient is left with a permanent leakage of cyanotic blood through the fenestration and into the oxygenated blood being pumped to the body. The patient experiences reduced exercise tolerance along with an increased risk of embolic stroke due to clots that may form in the venous system and and flow into the systemic circulation. Thus it is generally undesirable in the long term to create a permanent fenestration at the time of the Fontan procedure. However, as mentioned above, access to the heart is often required for certain treatments, and, if no communication exists an additional surgery may be required to facilitate the access and undertake the treatment or treatments of the heart.

When the approach of making a fenestration during the Fontan procedure is taken, the fenestration may spontaneously close, often within a short time after surgery. Further, in cases in which a fenestration is not made during the Fontan procedure, or when such fenestration has later closed, some patients experience intolerable elevation of venous pressure. An elevation of venous pressure is concomitant with the Fontan procedure because the venous system is not isolated from the back pressure due to the blood flow through the lungs as would be the case with a normal heart. Although tolerable in most cases, as mentioned above, in other cases complications can arise. These complications often include the collection of fluid in the chest and abdominal areas or malabsorption of nutrients from the gut. The indicated procedure in such cases is to intervene surgically to make or re-open a fenestration to, in effect, create a pressure relief to allow a bleed-off of venous blood from the graft into the heart and thus reduce the pressure. This procedure makes the patient more cyanotic at baseline, compromises the patient's exercise tolerance, and increases stroke risk. However, it may be considered acceptable as compared to the longer term effects of symptomatically elevated venous pressure. Moreover, where a fenestration was created during the Fontan surgery, it often later becomes advisable to close the fenestration. Closing the fenestration requires another difficult catheterization procedure.

In order to gain treatment access to the heart or to make a permanent fenestration after the Fontan procedure is completed, a venous catheterization is commonly used. A catheter equipped with a puncturing or cutting tool is threaded into the graft, the desired site of the fenestration is identified, and a puncture or opening is made through the wall of the synthetic graft and into the interior of the heart. There are significant difficulties in locating the proper site for making the opening. The difficulty is further magnified by the fact that the puncture may inadvertently be made in an area not immediately adjacent the heart thereby creating a leakage into the chest cavity that is difficult if not impossible to repair. Moreover, even when the puncture is made through the graft wall and directly through the immediately adjacent and contacting outer wall of the heart, there can be difficulties due to leakage if proper sealing is not accomplished.

There is a need for a vascular tube graft that can be implanted during a Fontan procedure and which allows easy, reliable, and repeated access to the heart without creating a permanent leak or fenestration.

SUMMARY OF THE INVENTION

The invention comprises an implant which may be implanted into a body. The basic form of the implant is that of a synthetic tissue having a wall with two sides. Disposed within the wall is a valve through which access may be gained from one side of the wall to the other side of the wall. When the implant is implanted into a body, the wall thereof separates two distinct areas within the body. When closed, the valve completely isolates the two areas from each other, and when opened the valve permits communication between the two areas separated by the implant. A marker forms a part of the implant and is disposed in close proximity to the valve. This marker may be visualized or otherwise located from outside the body. Locating the marker serves to precisely determine the location of the valve within the body.

In one embodiment, the synthetic tissue is in the form of a tubular graft. The tubular graft includes a wall structure having a valve incorporated therein. The valve may be alternately and from time to time placed in an open state, allowing communication across the valve, or a closed state, preventing communication there across.

A method of performing a Fontan procedure is described wherein the vascular graft is implanted to conduct returning venous blood to the pulmonary system. The vascular graft is connected between the venous system and the pulmonary system and is placed adjacent to the heart or through a portion of the heart. The graft is positioned and attached such that the valve permits interventional access through the valve into the heart.

Also the invention includes a method of gaining access to a part of the heart after a surgery in which the vascular graft has been implanted in the venous pathway and adjacent the heart. A surgical device is guided through the graft and through the valve and into a part of the heart. This method is useful, for example, when a patient suffers cardiac arrhythmias which require access to the heart for treatment.

The invention further includes a method for reducing the venous pressure of a patient who has undergone a Fontan procedure. A surgical device is guided through the graft to place the valve in a stable open state to allow bleed-off of excess venous pressure into the heart.

Other objects and advantages of the present invention will become apparent and obvious from a study of the following description and the accompanying drawings which are merely illustrative of such invention.

DETAILED DESCRIPTION

The present invention relates to a synthetic implant that can be surgically implanted into the body. While the form of the implant may vary, it will typically include a wall having a valve incorporated therein. The implant permits a surgical device to perform one or more treatments within the body. As used herein, the term "surgical device" means any device extended by a physician into any portion of a body to perform treatment procedures within on body. Surgical devices may, for example, include probes, cutting devices, stimulators, expanders, or clamps as well as catheter systems with which such devices may be inserted and navigated within the body. As will be discussed in more detail subsequently herein, a surgical device may be disposed on one side of the implant to be inserted through the valve in order to gain access to an area of the body on the opposite side of the implant. Thus, access may be gained without creating a permanent opening. In addition, while in many applications the valve is closed, the valve may be opened or held open to permit blood, for example, to pass through the valve.

One particular use of the implant is in conjunction with treating heart abnormalities. An example is congenital heart disease in infants, a significant manifestation of which includes heart malformation in which the heart comprises only one functional ventricular chamber. When used to treat this condition, the implant comprises a vascular graft which is surgically implanted to direct the venous return flow of blood to the lungs without permitting it to flow through the heart. The surgical procedure for obtaining this separation is well known and commonly referred to as a Fontan procedure, described in some detail in the Background of the Invention herein. Both in the immediate recovery period after a Fontan procedure as well as during long term care, it often becomes necessary to gain access to the heart for subsequent treatments. The device and methods of the present invention address gaining access to the heart for performing such treatments.

Figure 1:
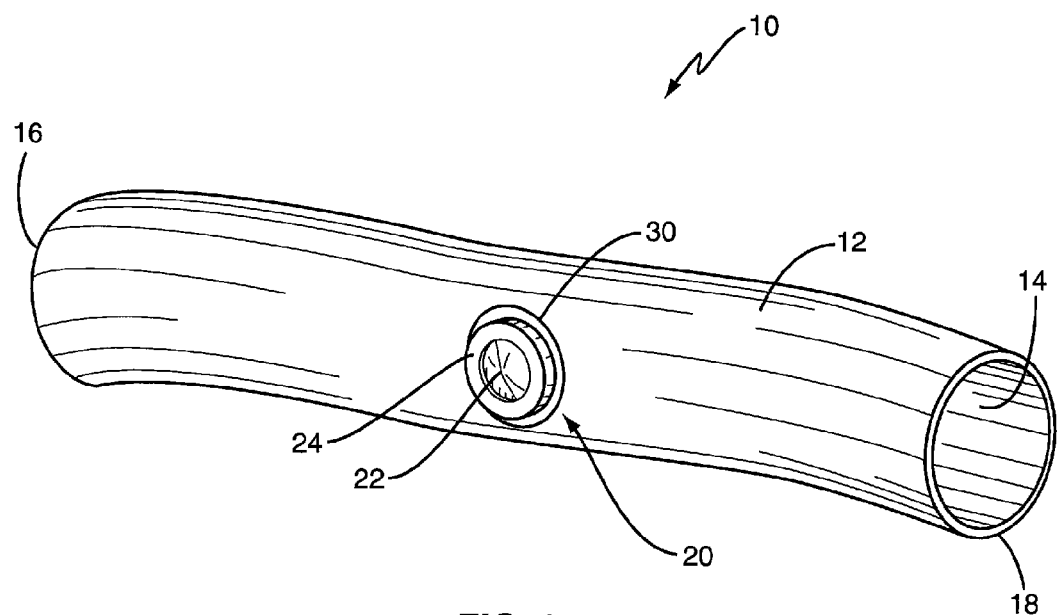
FIG. 1 is a perspective view of the vascular graft with a valve disposed within the wall thereof.

Turning now to a particular embodiment of the invention, and referring to FIG. 1, the implant comprises a vascular graft, indicated generally by the numeral 10. Vascular graft 10 is constructed from synthetic material and comprises a prosthetic device. Graft 10 assumes a generally elongated tubular shape and includes a wall 12 surrounding and bounding an interior 14. Vascular graft 10 further includes a proximal end 16 and a distal end 18, where the terms proximal and distal relate to the normal orientation of the graft when implanted within a body.

A valve, indicated generally by the numeral 20, is integrated into wall 12 of graft 10 to enable access and communication between interior 14 of the graft and areas outside the graft. Valve 20 may assume a stable closed state, preventing fluid flow there through, or it may be opened and left open to permit flow. Further, as discussed later, access to an area of the body may be gained by passing a surgical device through valve 20. Valve 20 includes a barrier 22 that, in a closed state, separates of interior 14 from areas outside vascular graft 10. When in a closed state, barrier 22 is generally impervious to fluids, in particular blood. Barrier 22 is capable of being penetrated or otherwise opened by explicit activation or operation to enable access there through from interior 14 to an area outside vascular graft 10. Barrier 22 may be made of various materials and substructures and may take the form of an elastomeric membrane. Such a membrane may include an opening which is held closed by internal elastic forces, or it may be penetrable and intrinsically re-sealable by the fundamental character of the membranous material used. Valve 20 further comprises a support 24 which generally surrounds and supports barrier 22. Support 24 includes a side 24A and may also be used to attach valve 20 to the implant and other structures. Support 24 and barrier 22 may be integrated or formed into wall 12 of graft 10 by any of a number of conventional fabrications, molding, or material treatment methods. Many valves used in medical applications employ features herein discussed and are adaptable to being formed within the wall of a synthetic implant such as vascular graft 10. On example of such a valve is a hemostatic valve. Hemostatic valves are designed to prevent blood flow except in special circumstances in which the hemostatic valve is opened to permit flow of blood. The simplest form of such a valve includes an impermeable elastomeric membrane stretched across an opening and sealing the opening. For such a valve, access across the valve is typically obtained by penetrating the membrane with a hollow needle through which fluids may then be allowed to pass. When the needle is retracted, the opening closes by elastic action within the membrane sufficient to render the membrane again impervious at typical fluid pressures.

Performing a Fontan procedure using vascular graft 10 of the present invention enables a surgeon to subsequently gain access to the heart through valve 20 as will be discussed in more detail herein. In order to gain access, valve 20 must be located. In one embodiment, a marker 30 is incorporated in the implant in the vicinity of valve 20. When marker 30 is located, because of its known position relative to valve 20, the valve may then be located. Marker 30 may be made in any shape and of any materials. Further, marker 30 may be integrally incorporated into valve 20 as a part, for example, of support 24. Alternatively, marker 30 may be attached to or incorporated within wall 12 of graft 10. Marker 30 further has properties or features which enable the marker to be visualized or otherwise located from outside the body. In one embodiment, marker 30 comprises a generally circular or ring element surrounding valve 20. Also in one embodiment, marker 30 includes a radio-opaque material which may be visualized fluorscopically from outside the body.

Figure 2:
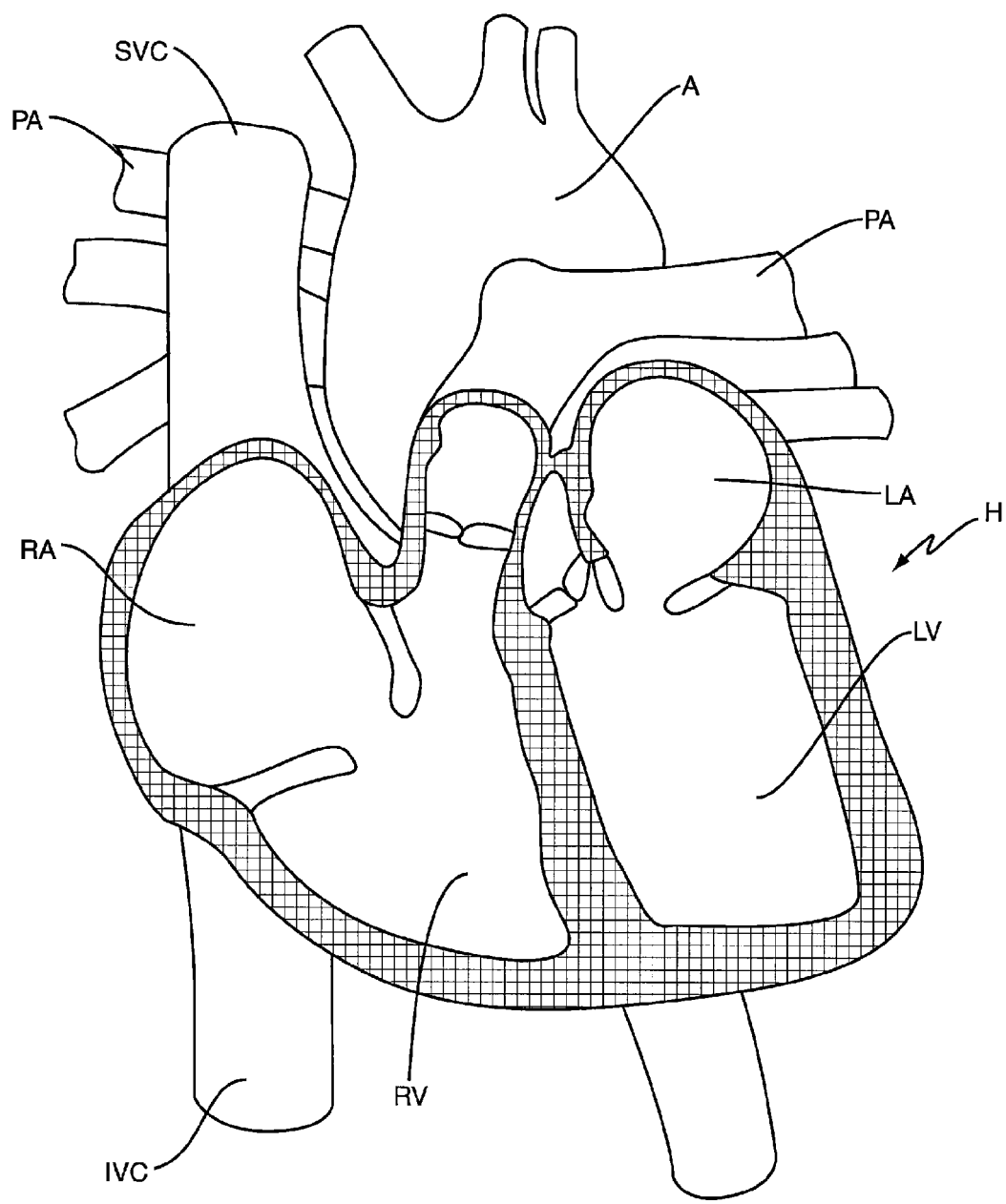
FIG. 2 is a sectional view of the normal heart showing the pumping chambers and the relevant vascular structures associated with the normal heart.

Turning now to implanting vascular graft 10, it is useful to revisit the discussion in the Background of the Invention while referring particularly to FIG. 2. The heart, indicated generally by the letter H, comprises four chambers to accomplish the pumping function of the heart. These chambers are the right atrium RA, the right ventricle RV, the left atrium LA and the left ventricle LV. Sequenced and rhythmic contraction of the atria followed by contraction of the ventricles produces the pumping action. The heart is further connected to the circulatory system by means of the superior vena cava SVC, the inferior vena cava IVC, the pulmonary arteries PA, and the aorta A. The pumping action of the heart H serves to force cyanotic or oxygen-depleted blood returning from the body into pulmonary arteries PA and thence to the lungs for re-oxygenation. The pumping action further serves to force oxygenated blood flowing from the lungs into aorta A and thence to all parts of the body. Considering now this pumping action in more detail, cyanotic, blood returning from the head and upper extremities of the body enters right atrium RA from superior vena cava SVC. The blood returning from the lower body and extremities enters right atrium RA from inferior vena cava IVC. Sequenced contractions of right atrium RA and right ventricle RV move the blood into pulmonary arteries PA and thence to the lungs as mentioned above. Oxygenated blood flows from the lungs into left atrium LA, and sequenced contractions of left atrium LA and left ventricle LV force the blood into aorta A and thence to all parts of the body. Blood moves through the tissues of the body, performing functions including oxygenation of the tissues, by means of progressively finer passages in the tissues known as capillaries. Blood moves from the tissues into the venous system through fine passages known as venules leading into the progressively larger veins and venae cavae SVC and IVC of the venous system. The blood in the veins moves back to the heart under action of the venous system as described in the background.

Numerous forms of congenial heart disease impair this circulation due to development of a heart with only one functional ventricle. These abnormalities are commonly addressed by a series of surgical procedures known collectively as the Fontan procedure. The Fontan procedure generally separates the venous or cyanotic return blood flow from the heart and reroutes the blood flow directly to the lungs as discussed above in the Background of the Invention.

The present invention includes vascular graft 10, a method for implanting the vascular graft consistent with the Fontan procedure, and a method for gaining access to the interior of the heart for post-operative short and long term medical care. The method for implanting vascular graft 10 is a modification of extant Fontan procedures. Vascular graft 10, when thus implanted, provides a way to repeatedly gain access to the heart through graft 10 and through valve 20.

Figure 3:
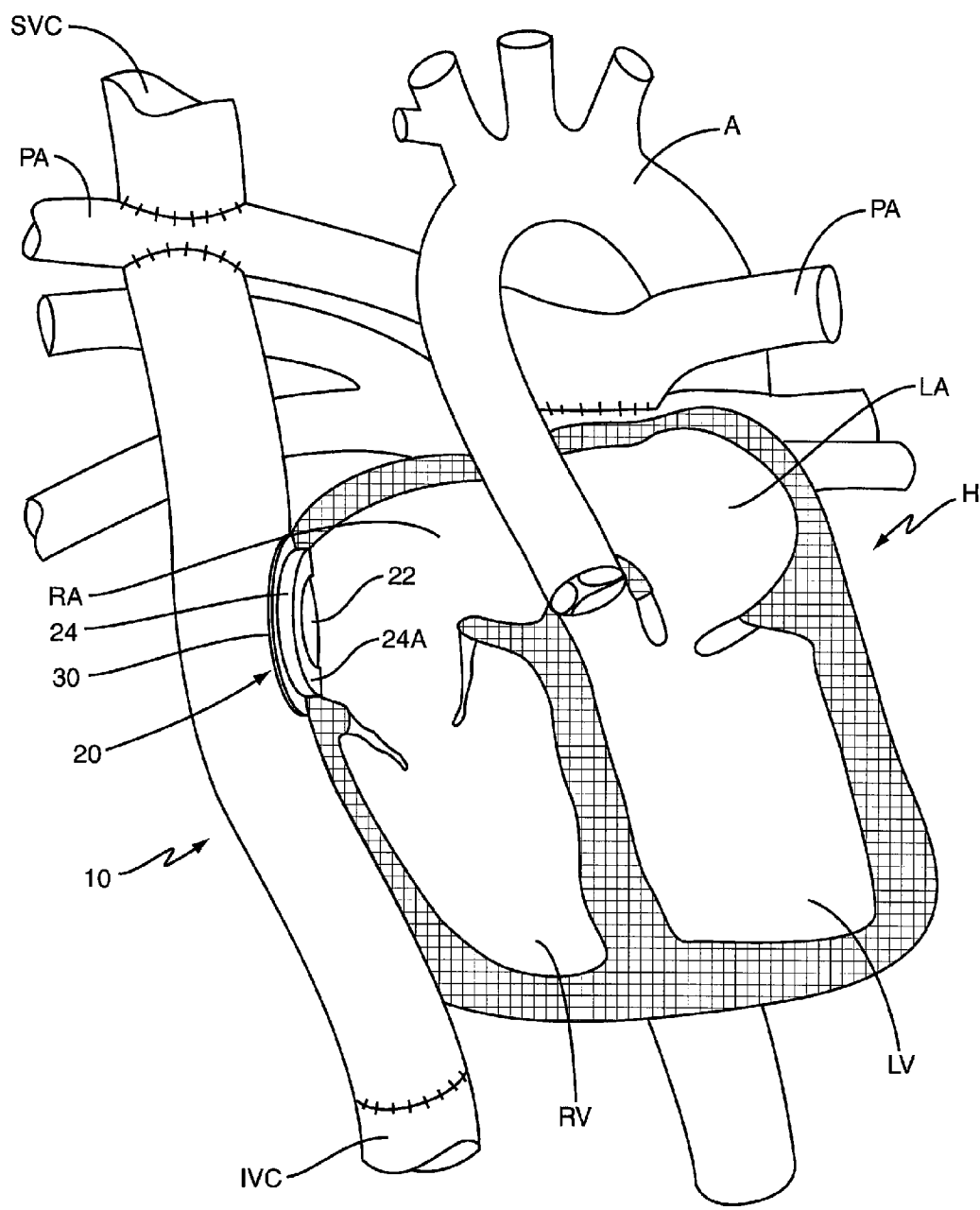
FIG. 3 is a sectional view of the heart with the vascular graft implanted according to the one form of a Fontan procedure.

FIG. 3 illustrates a heart that has undergone a Fontan procedure wherein vascular graft 10 has been implanted as a part of the Fontan procedure. It is appreciated that ventricular malformation may occur in either the right or left side of the heart, as discussed in the background. Hereinafter, the description will relate to a right side malformation, but it is to be understood that the description of the present invention does not differ for left or right side heart malformations. The specific form of Fontan procedure shown in FIG. 3 is an External Conduit Fontan as described in the Background of the Invention. In this case, vascular graft 10 is implanted outside the heart and connects inferior vena cava IVC to pulmonary arteries PA. The actual order of the steps described herein may not be the order in which they are actually performed in a particular surgery. Surgeon preferences and anatomic considerations particular to a given patient may dictate alternate orders for the steps. Typically, the patient is prepared for a Fontan operation through a series of preliminary procedures accomplished in one or more operations prior to the operation. This preparation is common to existing Fontan procedures, is well known to those of skill in the art, and is generally described in the Background of the Invention.

After appropriate preliminary surgery or surgeries, vascular graft 10, shown in FIG. 1, is implanted during the course of performing the Fontan operation. Vascular graft 10 is positioned relative to heart H such that side 24A of valve support 24 is in intimate contact with the heart. Side 24A may be pressed against the outside of heart H or it may be inserted within a surgical opening made in the heart and sized to fit support 24 of valve 20. By one of any number of means, for example, the use of sutures or surgical adhesives, valve 20 is attached and sealed to the heart. It is noted that an opening can be formed in heart H, and valve 20 can be secured to the opening. However, an opening in heart H is not required as valve 20 can be positioned and secured directly adjacent a portion of the heart. Proximal end 16 of graft 10 is connected to the inferior aspect of a branch of pulmonary arteries PA, at a location generally inferior to, or below, the attachment earlier made of superior vena cava SVC to the superior aspect of the branch of pulmonary arteries PA. Distal end 18 of graft 10 is surgically connected to inferior vena cava IVC which was removed from its attachment to heart H. Vascular graft 10 then lies alongside the heart and is entirely outside the heart. It is, however, connected to the heart at valve 20. Thus the entire venous flow of cyanotic blood returning from the body is separated from the blood flow through heart H, a part flowing from superior vena cava SVC directly into pulmonary arteries PA and another part flowing from inferior vena cava IVC through vascular graft 10 and into pulmonary arteries PA. This separated flow is directed through pulmonary arteries PA and thence into the lungs for re-oxygenation.

Figure 4:
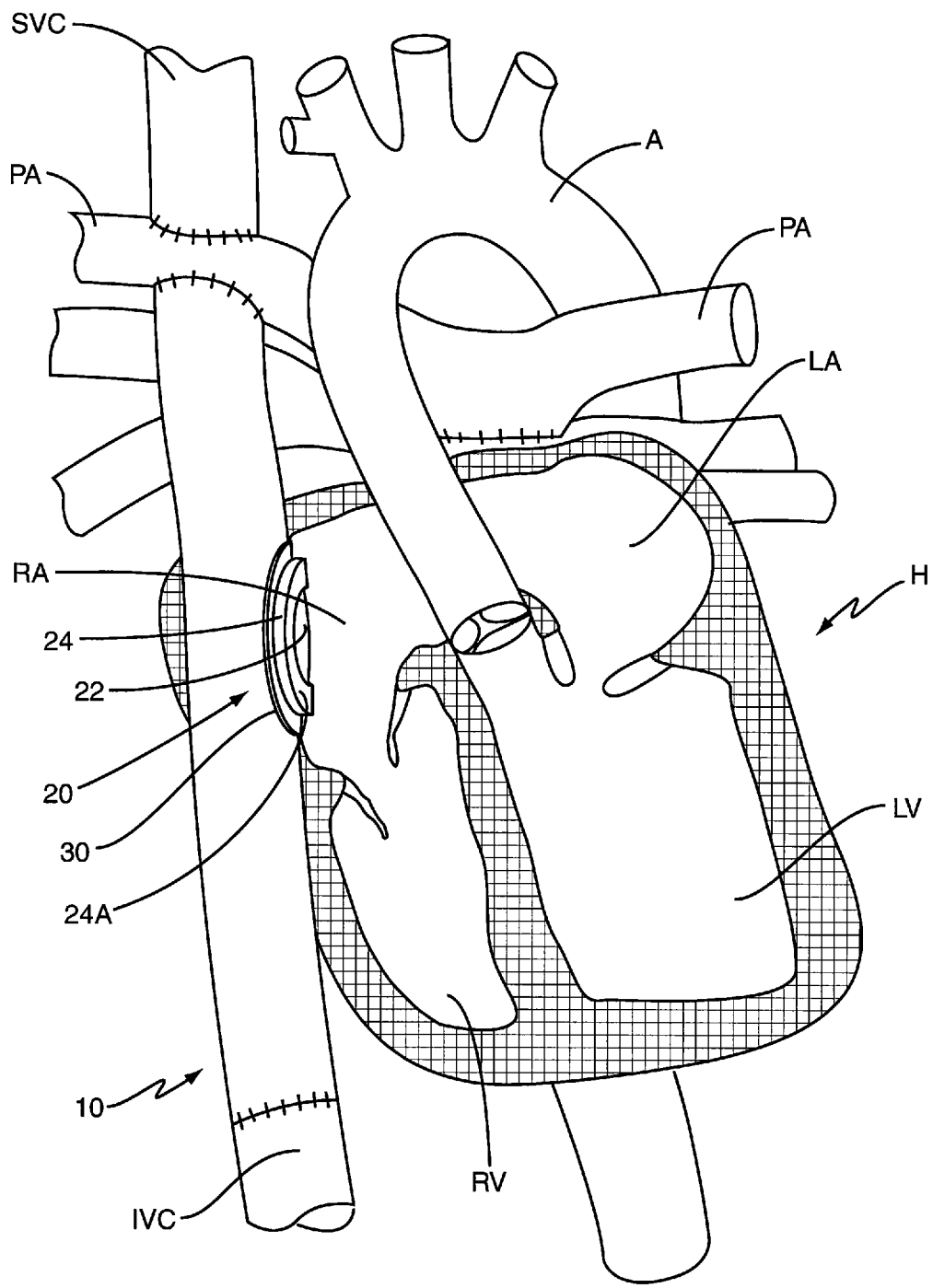
FIG. 4 is a sectional view of a portion of the heart with the vascular graft implanted according to another form of a Fontan procedure.

An alternative implantation of the vascular graft 10 of the present invention is depicted in FIG. 4. In this case vascular graft 10 is implanted in a tunnel surgically constructed in the heart in accordance with the well known Lateral Tunnel Fontan procedure as described in the Background of the Invention herein. The patient is first prepared in one or more preliminary operations which are generally as described above for the External Conduit Fontan procedure but for one difference. The difference is that a tunnel is surgically prepared generally on the right side of heart H through a portion of right atrium RA. Vascular graft 10 is thus positioned within heart H such that valve 20 is directed into right atrium RA such that side 24A is disposed within the atrium. Proximal end 16 is connected to the inferior aspect of pulmonary arteries PA and distal end 18 is connected to inferior vena cava IVC as has been earlier described herein.

Figure 5:
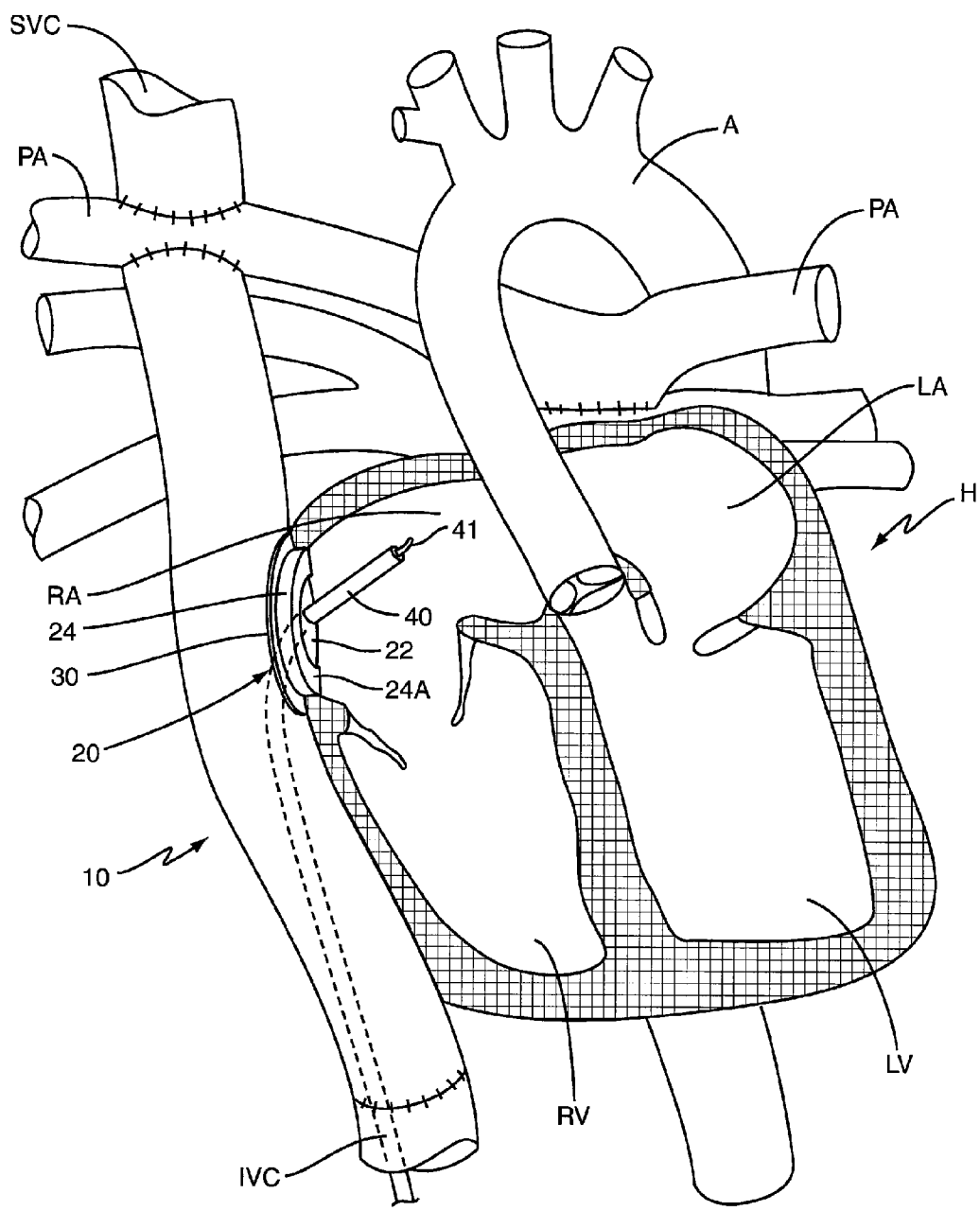
FIG. 5 is a sectional view of the heart after being subjected to a Fontan procedure employing the vascular graft, and showing a surgical device inserted through the graft and the valve into the heart.

The present invention also entails a method of gaining access to heart H from within vascular graft 10, one example of which is shown in FIG. 5. It is often necessary to gain access to the interior of the heart at various times subsequent to a Fontan procedure. Gaining such access is necessary to perform certain surgical treatments or other medical procedures. While the method is illustrated for a heart having been subjected to an External Conduit Fontan procedure, the following discussion thereof applies equally to a heart H that has been subjected to a Lateral Tunnel Fontan procedure. In order to gain access, a surgical device 40 is threaded into the venous system and into interior 14 of vascular graft 10. Surgical device 40 may be any instrument capable of being moved through the venous system by a catheter, for example. Marker 30, depicted in FIG. 5 as a radio-opaque ring disposed around valve 20, is located utilizing imaging equipment such as X-ray, fluoroscopy, or ultrasound in order to visualize the location of valve 20. While visualizing the marker 30 and the tip 41 of surgical device 40, tip 41 is positioned adjacent barrier 22 and penetrated there through and into heart H. Surgical device 40 may be adapted to perform one or more surgical procedures within heart H by employing various extant surgical implements disposed thereon. When the surgical procedures are completed, device 40 is withdrawn through barrier 22 and into the interior of vascular graft 20, and barrier 22 closes to prevent communication between the interior of the graft and heart H. Surgical device 40 is removed from graft 10 and withdrawn through the venous system to the outside of the body.

Figure 6:
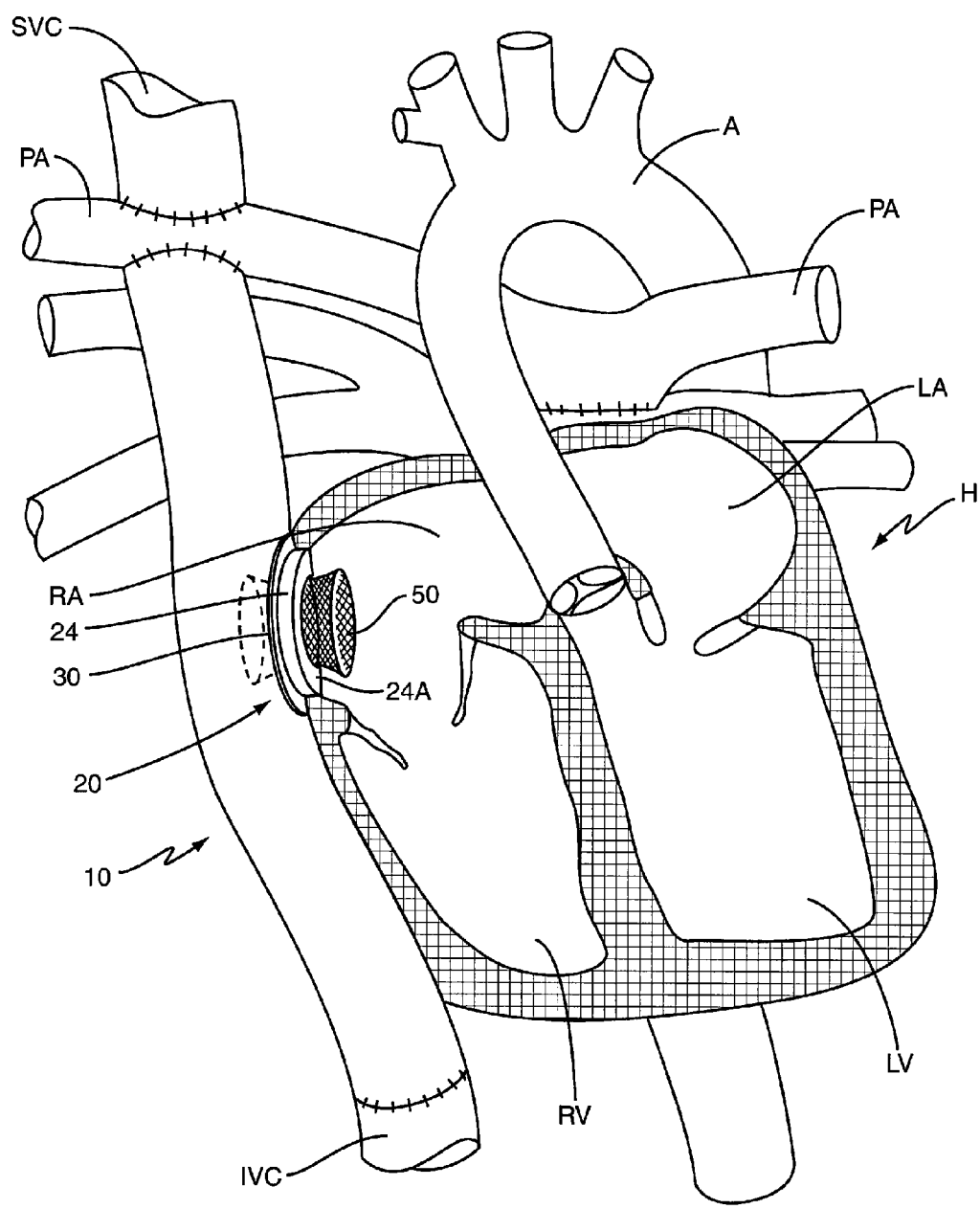
FIG. 6 is a sectional view of the heart after being subjected to a Fontan procedure using the vascular graft and showing a stent inserted through the valve and holding the valve in an open state.

As described above, referring now to FIG. 5, in one embodiment a surgical device may be used to perform various surgical interventions. In one case, surgical device may be used to implant a stent 50 in valve 20, the result of which is shown in FIG. 6. Inserting stent 50 unto the valve creates a fixed fenestration of a specific size. Stents of various sizes may be used to provide various sizes of fenestrations. Stent 50 can be delivered and inserted into valve 20 by conventional means. For example, catheter-based systems for stent implantation are well known and appreciated by those skilled in the art. These systems enable the delivery of a stent, collapsed for transport through the venous system, to the implantation site where it is inserted into an occluded passage and expanded to open the passage. In this case, the implantation site is valve 20, and the collapsed stent is inserted through barrier 22 and expanded, thereby holding the valve open and allowing fluid communication between graft 10 and heart H, allowing some portion of the return blood flow to vent into the heart. Further, should conditions later warrant discontinuing the venting of blood flow, removal of stent 50 may be accomplished by essentially reversing the process already described. It is appreciated that valves of various designs may be operable to be held in an open state by means other than the insertion of a stent. Moreover, various designs may be operable to provide varying sizes of openings. One of ordinary skill in the art will appreciate that placing valve 50 in an open state and returning the valve to the closed state may be done with various kinds of valves and by various means, and that the example discussed is but one of many approaches that can be used.

The present invention may, of course, be carried out in other specific ways than those herein set forth without departing from the scope and the essential characteristics of the invention. The present embodiments are therefore to be construed in all aspects as illustrative and not restrictive and all changes coming within the meaning and equivalency range of the appended claims are intended to be embraced therein.

The invention claimed is:

1. An implant for implanting in a body, comprising:
    a vascular graft having a generally elongated tubular shape and a wall defining an interior;
    a valve disposed in the wall, the valve including an elastomeric membrane barrier that is impermeable to fluids to prevent the communication of fluids though the valve, wherein the valve is configured to permit penetration of the elastomeric membrane barrier by a surgical instrument inserted through the valve from the interior of the vascular graft to enable access by the surgical instrument to an area external to the vascular graft; and
    a marker configured to allow location of the valve to facilitate penetration of the surgical instrument through the elastomeric membrane barrier.

2. The implant of claim 1, wherein the valve further comprises a support defining an opening, the elastomeric membrane barrier stretched across the opening by the support to seal the opening.

3. The implant of claim 2, wherein the marker is disposed within the support.

4. The implant of claim 1, wherein the marker is generally ring shaped and surrounds the elastomeric membrane barrier.

5. The implant of claim 1, wherein the marker comprises a radio-opaque material configured to be visualized fluoroscopically.

6. An implant configured for implantation during a Fontan procedure, comprising:
    a vascular graft configured to separate cyanotic blood flow from the heart and route this blood flow directly to the lungs, the vascular graft including a first end for attachment to the inferior vena cava, a second end for attachment to a pulmonary artery and a wall defining an interior;
    a valve disposed in the wall, the valve including an elastomeric membrane barrier that is impermeable to fluids to prevent the communication of fluids though the valve, wherein the valve is configured to permit penetration of the elastomeric membrane barrier by a surgical instrument inserted through the valve from the interior of the vascular graft to enable access by the surgical instrument to the heart; and
    a marker configured to allow location of the valve to facilitate penetration of the surgical instrument through the elastomeric membrane barrier.

7. The implant of claim 6, wherein the valve further comprises a support defining an opening, and wherein the elastomeric membrane barrier stretched across the opening by the support to seal the opening.

8. The implant of claim 7, wherein the marker is disposed within the support.

9. The implant of claim 6, wherein the marker is generally ring shaped and surrounds the elastomeric membrane barrier.

10. The implant of claim 6, wherein the marker comprises a radio-opaque material configured to be visualized fluoroscopically.

11. An implant for implanting in a body, comprising:
    a vascular graft having a generally elongated tubular shape and a wall defining an interior;

a valve disposed in the wall and including an elastomeric membrane barrier that is impermeable to fluids to prevent the communication of fluids though the valve, the valve configured to permit penetration of the elastomeric membrane barrier by a surgical instrument inserted through the valve from the interior of the vascular graft to enable access by the surgical instrument to an area external to the vascular graft, wherein the elastomeric membrane barrier is configured to close upon withdrawal of the surgical instrument from the valve so that the elastomeric membrane barrier remains at least substantially impermeable to fluids after withdrawal of the surgical instrument to prevent the communication of fluids though the valve; and a marker configured to allow location of the valve to facilitate penetration of the surgical instrument through the elastomeric membrane barrier.

12. The implant of claim 11, wherein the valve further comprises a support defining an opening, the elastomeric membrane barrier stretched across the opening by the support to seal the opening.

13. The implant of claim 12, wherein the marker is disposed within the support.

14. The implant of claim 11, wherein the marker is generally ring shaped and surrounds the elastomeric membrane barrier.

15. The implant of claim 11, wherein the marker comprises a radio-opaque material configured to be visualized fluoroscopically.

16. The implant of claim 11, wherein the surgical instrument comprises a stent configured to provide a fenestration to permit fluid flow through the valve.

* * * * *